United States Patent [19]

Sonenstein et al.

[11] 4,259,957
[45] Apr. 7, 1981

[54] FASTENING MEANS FOR DIAPERS

[75] Inventors: Gerard G. Sonenstein, Yardley, Pa.; James A. Kaeser, Somerset, N.J.

[73] Assignee: Colgate-Palmolive Company, New York, N.Y.

[21] Appl. No.: 888,717

[22] Filed: Mar. 21, 1978

Related U.S. Application Data

[63] Continuation-in-part of Ser. No. 634,978, Nov. 24, 1976, abandoned.

[51] Int. Cl.³ .......................... A61F 13/16; A41B 3/02
[52] U.S. Cl. ............................ 128/287; 128/DIG. 15; 2/DIG. 6
[58] Field of Search ............... 128/284, 287, DIG. 30, 128/DIG. 15; 24/204, 201 R, 201 HE, 8; 2/DIG. 6

[56] References Cited

U.S. PATENT DOCUMENTS

| 1,268,075 | 5/1918 | Glynn | 24/204 |
| 2,685,879 | 8/1954 | Emmet | 128/287 |
| 3,081,772 | 3/1963 | Brooks et al. | 128/287 |
| 3,235,926 | 2/1966 | Mates | 24/204 |

OTHER PUBLICATIONS

Merriam-Webster's Collegiate ® Dictionary, 1977 edition, pp. 600, 1279–1280.

Primary Examiner—Robert W. Michell
Assistant Examiner—C. W. Shedd
Attorney, Agent, or Firm—Norman Blumenkopf; Herbert S. Sylvester; Murray M. Grill

[57] ABSTRACT

A diaper comprising a rectangular body of absorbent material having apertures in the corners thereof. Fasteners having hook-like filaments of "Velcro" material are attached to the diaper by hooks integrally formed with the "Velcro" filaments and engaged in the apertures of the diaper.

1 Claim, 3 Drawing Figures

U.S. Patent    Apr. 7, 1981    4,259,957
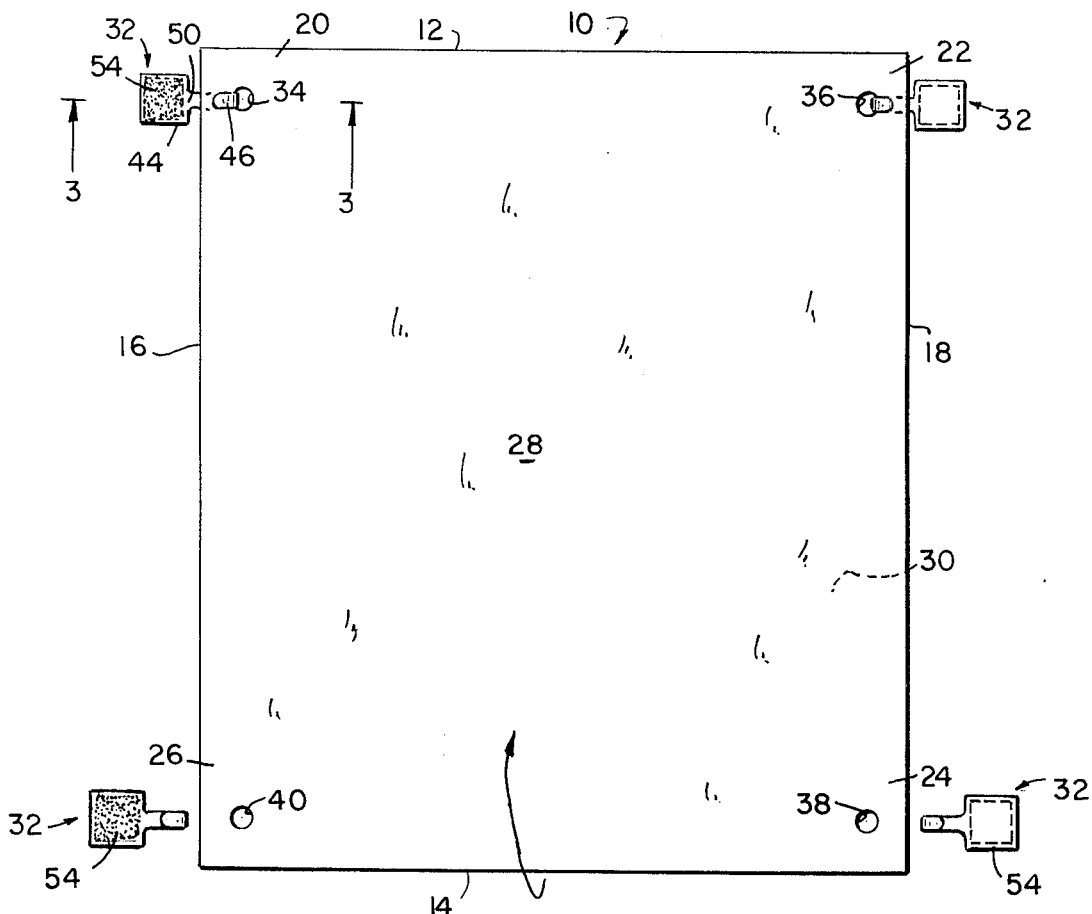
FIG. 1
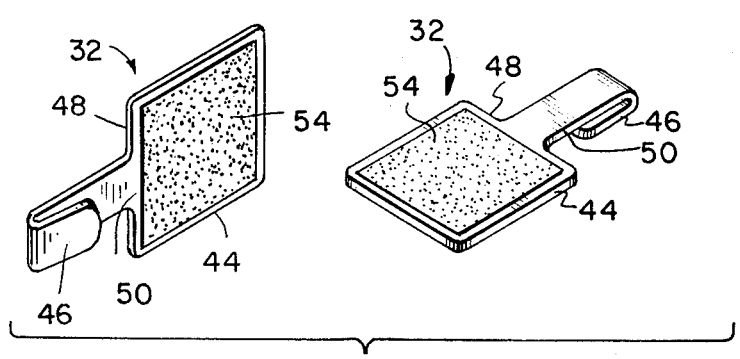
FIG. 2
FIG. 3
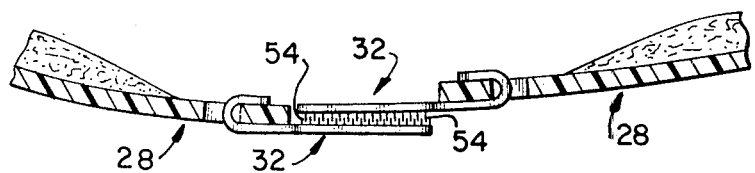

FASTENING MEANS FOR DIAPERS

REFERENCE TO RELATED APPLICATION

This application is a continuation-in-part of the application of Gerard G. Sonenstein and James A. Kaeser, Ser. No. 634,978, filed Nov. 24, 1976, for "Improved Fastening Means for Diapers", now abandoned.

BACKGROUND OF THE INVENTION

1. Field of the Invention

This invention relates to improved fastener means for diapers of either the disposable or non-disposable type and more particularly to improved fastener means enabling the diaper to be adjustably fitted about the trunk of an infant.

2. Description of the Prior Art

Conventional diapers of the permanent or non-disposable type generally comprise an essentially rectangular, absorbent sheet material, such as cloth, defined by opposed lateral and longitudinal edges, the juncture of the edges defining four corner portions.

Various types of fastener devices enabling closure of the diaper about the trunk of an infant clad therewith are known in the art. These include pins or equivalent means having pointed portions which may present a definite safety risk to the infant—not to mention the inherent discomfort.

Similar problems are encountered with diapers of the disposable type which generally comprise a multilayer or laminate material having in order, a hydrophobic outer sheet, an absorbent core sheet and a fluid pervious facing sheet, the various sheets being bonded into an integral laminate structure by suitable adhesive means for example.

In addition to the aforementioned pin-type fasteners, other types of closure devices heretofore recommended for disposable or non-disposable diapers included various types of adhesive strips which are detachably secured to predetermined areas of the diaper, closure of the diaper being effected by contacting mating surfaces of the strips having sufficient tack to enable secured closure about the infant. Velcro ® strips have also been used.

However, fasteners of the foregoing types are found to have certain disadvantages. Thus, those types of fasteners designed for permanent attachment to the diaper often become deteriorated or otherwise impaired due to the often destructive effects of laundering, i.e., temperature, alkalinity, etc. Moreover, metallic parts are subjected to corrosion, rusting, and the like. In addition, as a practical matter, fastener devices of the safety pin-type are often difficult to manipulate and may become easily lost under the conditions of use as by sliding down in a sink drain. By contrast, those types of fasteners designed for temporary attachment to the diaper, as by adhesive bonding, have a tendency to chafe the infant causing severe skin irritation when the diaper, through movement of the infant, slips down the body. Pressure sensitive adhesive type fastener tabs are described, for example, in U.S. Pat. No. 3,776,234.

SUMMARY OF THE INVENTION

A primary object of the invention is to provide improved fastener means for diapers of the disposable or non-disposable type wherein the foregoing disadvantages are eliminated or at least mitigated to a substantial extent.

A further object of the invention is to provide fastener means for diapers which can be easily and efficiently manipulated to obtain a close, comfortable fit about the trunk of an infant.

A still further object of the invention is to provide fastener means for diapers wherein the risk of skin chafing or other forms of discomfort to the infant is greatly reduced.

Another object of the invention is to provide improved fastener means for diapers wherein essential cooperating fastener components can be removed from or attached to the diaper as desired by the user, e.g. prior to laundering.

Yet another object of the invention is to provide fastener means for diapers devoid of metallic parts and wherein problems associated with corrosion, rusting, and the like are substantially eliminated.

Still another object of the invention is to provide fastener means for diapers adapted to be readily, securely held by the user and wherein the risk of loss is greatly reduced.

Other objects and advantages of the invention will become more apparent hereinafter as the description proceeds.

The foregoing objects are attained in accordance with the invention which in its broader aspects provides a diaper comprising a body of absorbent material defined by opposed lateral and longitudinal edges, the junctures of said edges defining four corner portions, the diaper having an inner surface for direction toward the body of an infant and an outer surface facing away from the infant, each of the corner portions of a first lateral edge having first cooperative fastener means comprising a first strip of material detachably mounted on the outer surface of the diaper, the strip material having an inner and outer surface, the inner surface having a first portion comprising means for detachably securing said strip material to said diaper and a second portion comprising a myriad of finely woven filaments formed into permanent hooks, said second portion extending substantially outwardly of the longitudinal edge of said diaper, each of the corner portions of a second lateral edge having second cooperative fastener means comprising a second strip material having an inner surface attached through the outer surface of said diaper and an outer surface comprising a myriad of finely woven filaments formed into permanent hooks for detachably engaging the filaments of said first cooperative fastener means.

The invention is described in the following disclosure considered with the accompanying drawings wherein:

BRIEF DESCRIPTION OF THE DRAWING

FIG. 1 is a plan view of a diaper according to the present invention;

FIG. 2 is a perspective view of a fastener constructed in accordance with the present invention; and FIG. 3 is partial sectional view showing how the diaper is fastened.

DETAILED DESCRIPTION OF THE INVENTION

With continuing reference to the accompanying drawing wherein like reference numerals designate similar parts throughout the various views, reference numeral 10 generally designates a diaper in accordance with the present invention. The diaper is shown as being substantially rectangular in shape and has opposed longitudinal edges 12 and 14 and opposed lateral edges 16 and 18, the juncture of these edges forming corner portions 20, 22, 24, 26. The diaper has an inner surface 28 for direction toward the body of an infant and an outer surface 30 for direction away from the infant. Fastener means generally indicated at 32 are engageable in apertures 34, 36, 38, and 40 and each fastener means generally comprises a strip material portion 44 integrally formed with a hook 46. The strip portion 44 has an outer surface 48 and an inner surface 50. The inner surface 50 has an area 54 comprising a myriad of finely formed filaments formed into permanent hooks which have heretofore sold under the trademark Velcro ®. The fastener means 32 can be formed of a suitable resin, such as ethylene, propylene, nylon, or the like. Materials of the Velcro ® type are described in U.S. Pat. No. 2,717,437.

The diaper is positioned about the infant as shown in FIG. 2 in the drawing and the filaments facing each other are pressed together adjustably securing the diaper in place. If the diaper is of the disposable type, the fasteners may be detached from the diaper and the diaper thrown away. Alternatively, the fasteners can be detached from the diaper and the diaper easily washed with the fasteners being useful for either another disposable or reuseable diaper.

What is claimed is:

1. A disposable substantially rectangular multilayer diaper comprising a water impervious outer layer, an absorbent core layer and a water pervious inner, layer, said inner layer forming an inner surface for direction toward the body of an infant, said diaper being defined by opposed lateral and longitudinal edges, the junctures of said edges further defining four corner portions, said corner portions each having an aperture therein which is detachably engagable by mating first and second cooperative fastener means, each of said fastener means is comprised of an integral combination of an engagement member and a securement strip, said members being fabricated from a hard tooling polymeric resinous material so as to be generally T shaped and having an inward and an outward facing surface; the stem of said T shaped member being formed into a hook member which protrudes from the inward facing surface of said engagement member; said securement strip comprising a myriad of finely woven filaments which are formed into permenent hooks, and said strip is attached to the inward facing surface of said T shaped member of said first fastener means and is approximately coterminous with the cross-bar portion of said T shaped member; when said hook member of said first fastener means is engaged in said apertures, the cross-bar of said T shaped member is positionable so as to extend substantially outward from each corner portion of a lateral edge of said diaper; said strip is attached to the outward facing surface of said T shaped member of said second fastener means and is approximately coterminous with the cross-bar portion of said T shaped member; said second fastener means also being positionable so as to extend substantially outward from each corner portion of a second lateral edge, said strips on said first and second fastener means being detachably engageable so as to provide a securement of said diaper about the body of a wearer of said diaper.

* * * * *